United States Patent [19]

Azad et al.

[11] 4,434,150
[45] Feb. 28, 1984

[54] IMMUNOLOGICAL REAGENTS EMPLOYING POLYMERIC BACKBONE POSSESSING REACTIVE FUNCTIONAL GROUPS

[75] Inventors: A. R. M. Azad, Stoughton; Stefan J. Kirchanski, Framingham; Michael C. Brown, Wayland, all of Mass.

[73] Assignee: Ortho Diagnostic Systems, Inc., Raritan, N.J.

[21] Appl. No.: 313,019

[22] Filed: Oct. 19, 1981

[51] Int. Cl.$^3$ .................... G01N 33/54; A61K 43/00; A61K 49/00
[52] U.S. Cl. ..................... 424/1.1; 424/78; 424/81; 424/83; 435/4; 435/7; 436/518; 436/530; 436/823; 252/645; 128/1.1
[58] Field of Search ................ 424/1, 1.5, 8, 12, 1.1, 424/9, 85, 88, 78–83; 436/518, 528–532, 85, 804, 823; 435/4, 7; 252/301.1 R; 128/1.1

[56] References Cited

U.S. PATENT DOCUMENTS

| | | | |
|---|---|---|---|
| 3,641,235 | 2/1972 | Weiss | 424/8 |
| 3,652,492 | 3/1972 | Kamogawa et al. | 260/41 |
| 3,761,357 | 9/1973 | Epton et al. | 195/63 |
| 3,764,477 | 10/1973 | Lehmann et al. | 195/63 |
| 3,853,987 | 12/1974 | Dreyer | 424/1 |
| 3,857,931 | 12/1974 | Hager | 424/12 |
| 3,970,597 | 7/1976 | Sokolovsky et al. | 260/72 N |
| 3,996,345 | 12/1976 | Ullman et al. | 424/12 |
| 4,035,316 | 7/1977 | Yen et al. | 260/2.5 B |
| 4,108,972 | 8/1978 | Dreyer | 424/1 |
| 4,166,105 | 8/1979 | Hirschfeld | 424/8 |
| 4,169,137 | 9/1979 | Hirschfeld et al. | 424/8 |
| 4,174,384 | 11/1979 | Ullman et al. | 424/8 |
| 4,199,559 | 4/1980 | Ullman et al. | 424/8 |
| 4,220,722 | 9/1980 | Rowley et al. | 435/188 |
| 4,225,784 | 9/1980 | Barrett | 250/303 |
| 4,228,237 | 10/1980 | Hevey et al. | 435/7 |
| 4,231,999 | 11/1980 | Carlsson et al. | 424/1 |
| 4,254,096 | 3/1981 | Monthony et al. | 424/8 |
| 4,267,234 | 5/1981 | Rembaum | 428/403 |

FOREIGN PATENT DOCUMENTS 1107644 8/1981 Canada ................ 167/37
2963 7/1979 European Pat. Off. .

Primary Examiner—Benjamin R. Padgett
Assistant Examiner—M. Moskowitz
Attorney, Agent, or Firm—M. A. Hofer

[57] ABSTRACT

An immunological substance detecting reagent is provided which, in the preferred embodiment, employs an immunological homolog specific for the immunological substance to be detected coupled to a water-soluble polymer having a net charge not greater than zero. The water-soluble polymer further has associated a plurality of marker substances such as fluorophore molecules thereby providing a reagent of increased sensitivity for the detection of an antigen-antibody immunological reaction.

16 Claims, 6 Drawing Figures

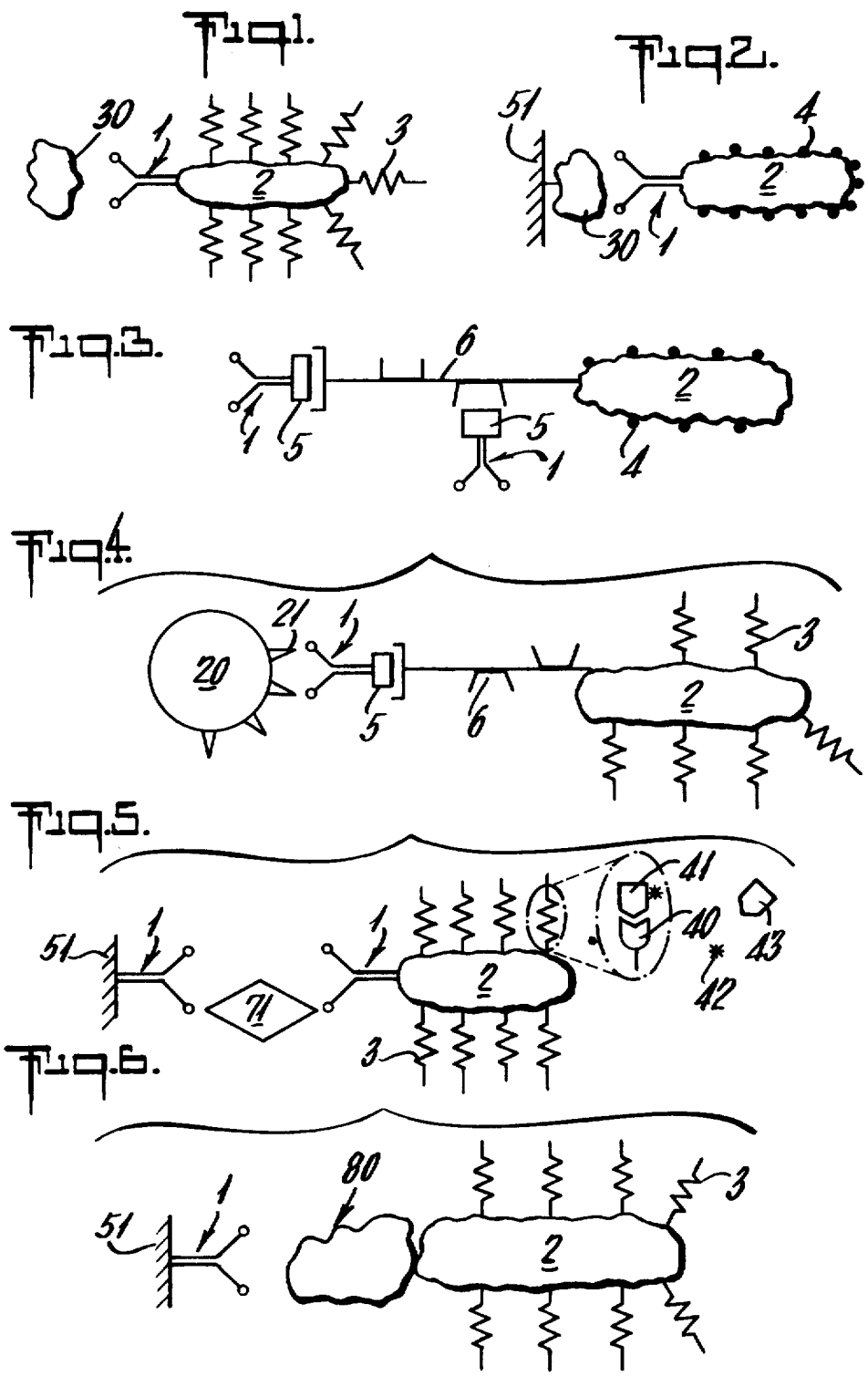

IMMUNOLOGICAL REAGENTS EMPLOYING POLYMERIC BACKBONE POSSESSING REACTIVE FUNCTIONAL GROUPS

FIELD OF THE INVENTION

This invention relates to the field of immunoassays and more specifically, describes an immunoassay reagent formed by the coupling of an immunological homolog specific for the immunological substance to be detected, to a water soluble polymeric backbone capable of further attachment to marker substances.

BACKGROUND OF THE INVENTION

The detection of foreign substances in body fluids is often essential to the proper diagnosis of a diseased state and selection of the appropriate treatment therefor. The foreign substances, generally termed antigens, may have associated therewith the capacity to stimulate the formation of a corresponding antibody which reacts specifically with that antigen. The antibody itself is a protein that is formed in response to the presence of an antigen for reaction with that specific antigen. Antibodies comprise a special group of serum proteins called immunoglobulins. Although the group of antibodies comprises a restricted group of proteins that are capable of specifically reacting with antigens, there is an enormous variety of macromolecules capable of behaving as antigens, including proteins, many polysaccharides, neucleoproteins, lipoproteins, numerous synthetic polypeptides as well as many other small molecules, called haptens, when they are suitably linked to proteins or synthetic polypeptides.

The specificity of antibody-antigen reactions has been utilized in the diagnosis of pathological states or physiological conditions and more particularly, in the detection of antigenic determinants. As used herein, the phrase "immunological substance" shall be defined as either an antibody or an antigen while the phrase "immunological homolog" shall be defined as the complement of the immunological substance which is capable of specific reaction therewith. Consequently, if the immunological substance being discussed is an antibody, then the immunological homolog would be the antigen for which that antibody is specific. The converse is equally contemplated.

In accordance with the knowledge of those skilled in the art, antigen-antibody reactions can be manifested by enzyme immunoassay, radioimmunoassay, or immunofluorescence techniques with high sensitivity; however, in large part, these techniques are limited to the sensitivity of typically complex instrumentation designed to locate and quantify the marker substances employed.

A well known class of prior art techniques for detecting an antigen-antibody reaction involved labeling the antibody with a tag or marker substance. This technique, however, possesses several disadvantages. The antibody protein is a very sensitive protein whose reactivity, the capability of selectively reacting with its immunological homolog present even in small concentrations, can be easily destroyed by the chemical addition of marker substances to the protein, i.e., denaturation. Further problems include the inability to attach a sufficient concentration of weakly fluorescent but desirable dye molecules such as the red excited fluorescent dye in order to get into a detectable range. On the other hand, if too many dye molecules are attached, then, even though denaturation of the antibody may not occur, nonspecific staining is likely because of the hydrophobic nature of the antibody-dye complex. Additionally, the loss of specificity occasioned by the presence of cationic charges, present on many dyes, makes such a system undesirable.

The concentration at the site of an immunological reaction of a marker substance (and thus the sensitivity of detection) may be increased by employing an indirect staining technique wherein a second immunoglobulin, directed against the first immunoglobulin, carries several dye molecules attached in normal fashion. Since the second immunoglobulin is typically heterospecific, i.e., it binds to several sites, the attachment of several second immunoglobulins to the first is possible. Consequently, the attachment of significantly greater numbers of dye molecules onto the first immunoglobulin, specific against the antigen to be detected, increases the antigen detection sensitivity. Unfortunately, such a procedure involves two reaction steps making it unsuitable for facile use in automated instrumentation. Additionally, while the second antibody system does increase detection sensitivity, it still suffers from the same limitations present in the directly labelled antibody system first described.

It is an object of the present invention to minimize the loss of reactivity and sensitivity due to nonspecific binding occasioned by the above methods.

Another class of well-known prior art techniques employs a biotin-avidin complex which binds by physical adsorption. Although biotin-avidin does not result in a covalent bond, is nonetheless exhibits a very high binding constant. The biotin is, in relation to the antibody, a comparatively small molecule so that the antibody is capable of carrying a number of biotin molecules on its surface. The addition of several labelled avidins to biotinylated antibody results in specific adsorption thereby yielding labelled antibody. Because the avidin is also a small molecule, less than half the size of an antibody, the amount of dye that can be attached to the avidin is limited. It is an object of the present invention to eliminate this limitation and still enjoy the advantages presented by employment of the biotin-avidin technique for linking an antibody to another substance.

Further attempts to increase the sensitivity of immunological reaction detection systems have employed the substitutions of radioisotopes for dyes. Radioisotopes are physically small labels and thereby minimize steric hindrances and sensitivity losses and permit the most sensitive level of detection. The use of radioisotopes, however, presents numerous disadvantages including the relatively short life of gamma emitting isotopes, e.g. $^{125}$I, the impairment of immunological reactivity by gamma radiation of the isotope, health hazards involved in the use of dangerous radioisotopes necessitating the use of procedures complying with federal standards, as well as requiring precise safety controls in addition to expensive, complex detection instrumentation. Further, the radioimmunoassay while suitable for soluble antigens is not readily adaptable on a cell by cell basis since it is really an averaging technique. To make the radioimmunoassay sensitive to a single cell for automated flow cytometry instrumentation would require advanced radiographic techniques. Such techniques would be expected to be slow and procedurally very complex. As a result, radioisotopes are generally nonsuitable for individual cell analysis. It is an object of the present invention to provide a reagent which will increase the sensitivity of autoradiographic techniques and radioimmunoassays and to decrease the possibility of radiation damage normally caused by direct labelling due to close physical proximity of the radioactive label to the antibody.

Enzymes, used in substitution for dye marker substances, advantageously provide an improvement in sensitivity due to the great turnover of substrate. Although such a system requires additional steps beyond the use of the typical dye marker substance, there is no photobleaching problem as evidenced with the use of fluorescent dyes. Furthermore, propitious choice of the enzyme permits the production of a colored compound or an acid readily discerned and quantified by automated equipment. Disadvantages include the large and sticky nature of enzymes which often results in denaturation of the antibody, and a loss of specificity due to the inherent nature of enzymes for nonspecific attachment or steric hindrance from homolog binding. Furthermore, enzymes present shelf life problems which reduce their effectiveness for practical use in clinical environments. If specific structures on the cell are to be localized or measured, then the substrate must precipitate directly on the cell in a conveniently detectable form, e.g., a fluorescent compound. A problem generally encountered with enzyme systems is a limitation in sensitivity because of a fixed and limited enzymatic rate. Compensation can be made for this by simply waiting longer for the enzyme to continue to act upon the substrate. This, of course, reduces the efficiency of such a technique in clinical applications and its usefulness in automated procedures where system throughput capability is of paramount importance. It is an object of the present invention to provide a reagent, compatible with enzymes, for detecting immunological reactions with increased sensitivity.

Electron opaque stains have found useful application in electron microscopy, however, such a system is far more complex and requires lengthy procedures thereby effectively eliminating its clinical value. To some degree, this disadvantage is compensated by an increase in resolution. Electron opaque stains include ferritic compounds, i.e., proteins containing iron or colloidal gold, however, it is noted that these compounds may be larger than the antibody and may therefore be expected to deleteriously affect the antibody's reactivity. It is an object of this invention to reduce such an effect on the antibody as well as to provide a reagent that is electronically dense and opaque to electron scanning.

Traditional attempts to overcome many of the above-described problems include the use of polymer particles or microspheres containing fluorescein or other marker type substances. Generally these polymer particles are constructed in the range of 50-2000 nanometers and consequently, the number that can be attached to a cell through an antibody is sterically limited. Tyically, the particles are coated with large numbers of antibodies; however, due to the physically large nature of the reagent, there is a greatly reduced chance of the antibody approaching an antigenic site on the cell in an appropriate orientation to result in the immunological reaction. Traditionally, the polymer particles have been made from styrenes and vinyl monomers by emulsion polymerization; however, the resulting hydrophobic particles disadvantageously exhibit nonspecific binding as well as colloidal instability. The latter instability is aggravated by the attachment of antibodies on the particle's surface. Of further disadvantage is the surface denaturation affect on the antibody following attachment of the antibody on the surface of the microsphere.

Attempts have been made to overcome the hydrophobic nature of polymeric particles by the incorporation of hydrophilic monomers into the particles, however, these attempts have been limited to emulsion polymerization procedures. Although alteration of the composition of the particles can improve nonspecific binding and colloidal instability problems, these undesirable characteristics cannot be completely eliminated since a minimal amount of hydrophobic monomer is required in order to synthesize the polymeric particle. One such polymeric particle detection system is described in U.S. Pat. No. 4,254,096 to Monthony et al wherein an assay method is described using antibodies covalently bound to hydrophilic polymeric particles which are water-insoluble, an undesirable characteristic. Even in the case of completely hydrophilic monomers, cross-linking agents are needed in order to make a hydrophilic particle as described in U.S. Pat. No. 3,853,987 to Dreyer. It is an object of the present invention to eliminate the requirement for a cross-linking agent.

Hirschfeld and Eaton describe another technique to increase sensitivity using a polymeric backbone in U.S. Pat. No. 4,169,137. They specifically describe an antigen detecting reagent consisting of a primary amine containing, polyfunctional polymeric backbone, i.e., polylysine, having coupled therewith a plurality of fluorescent dye molecules. The polyfunctional backbone was covalently bound through the primary amine on the polylysine to a primary amine moiety on the antibody by the use of a dialdehyde such as glutaraldehyde. Although such a method results in greater sensitivity per antigen site, serious limitations are presented by the described methodology. Specifically, the polymer is restricted to a primary amine containing polymer which, because of its cationic charges, exhibits strong nonspecific binding thereby greatly reducing its specificity. In fact, it was found that the type of polymer described by Hirschfeld attached to cells even without an antibody. Of further disadvantage is the requirement of a dialdehyde coupling reagent. These restrictions serve to drastically limit the advantageous attachment of various fluorescent dyes to the polymeric backbone. Also, the employment of a dialdehyde does not permit the attachment of nonprimary amine containing polymeric backbones to an antibody. When employed within the pH ranges of interest for biological applications, the described system tends to be cationically charged and therefore attaches nonspecifically, by electrostatic interaction, to anionically charged cell and tissue surfaces. Due to the unstable nature of the dialdehyde formed, covalent linkage and the reversible dialdehyde reaction, it is expected that Hirschfeld's reagent will contain much disassociated polymer and antibody capable of competitively reacting with antigenic sites and thereby reducing the sensitivity of the assay.

It is an object of the present invention to provide an immunological substance detection assay employing a water-soluble polymer to carry many detectors, and to avoid nonspecific attachment due to hydrophobic and cationic charge characteristics as well as to avoid the need for dialdehyde linking agents.

It is another object of the present invention to provide a reagent capable of detecting an immunological substance with increased sensitivity. It is a further object to avoid the problems associated with hydrophobic polymers and particles and cationically charged complexes which disadvantageously result in nonspecific binding by providing properly charged polymers having minimum hydrophobic characteristics. It is an object to provide a water-soluble polymer, capable of carrying a plurality of marker substances, which does not have a net positive charge.

It is yet another object to provide a reagent capable of simple storage and effective use in automated instrumentation. It is a still further object to provide a reagent capable of employing the desirable, but weakly fluorescent, red excited fluorescent dyes in concentrations and amounts capable of being detected with the technology presently employed in automated cytology instrumentation.

It is a yet further object to employ a water-soluble polymer in combination with avidin-biotin in order to utilize the individual advantages of each within a single reagent.

SUMMARY OF THE INVENTION

The principles of the present invention broadly employ direct and indirect marker techniques to aid in the detection of an immunological reaction wherein an immunologic homolog, specific for the substance to be detected, is bound, through a variety of intermediate mechanisms, to water-soluble polymers serving as or carrying detectable marker mechanisms. It is to be understood that the term water-soluble polymer, as used herein, encompasses that meaning as it is used in the conventional organic chemistry sense and does not include what is typically known in the art as microspheres which requires covalent cross-linkages or particles which are water-insoluble (hydrophobic) polymers. Consequently, a covalent cross-linking agent is not needed in the present invention. Typically, the invention embraces single chain polymers having a weight up to approximately $1 \times 10^7$ daltons and up to approximately $1 \times 10^9$ daltons for branched polymers.

Branched polymers encompass water-soluble polymers which contain a polymeric 'backbone' chain having a plurality of additional polymeric chains, composed of the same or different monomers, covalently attached anywhere along the length of the 'backbone' chain. A useful analogy for a branched polymer would be to a wire bristle brush which may or may not have missing bristles.

In accordance with the stated objects, the principles of the present invention embrace several embodiments of immunological substance detecting reagents employing a water-soluble polymer. All embodiments provide for charge specification but differ whether the charge of the polymer, the charge of the polymer having a marker substance attached to form a polymer-marker substance complex, or the charge of the polymer-marker substance complex with means for attaching to the antibody is specified. All embodiments include means for attaching the polymer to the homolog.

Additional embodiments have the attaching means selected from the group consisting of activated groups on the immunological homologs, activated coupling reagents, activated groups on the polymer, activatable groups on the polymer, and biotin-avidin complex wherein the avidin is bonded to the polymer and the biotin is bonded to the immunological homolog. Additional embodiments may further comprise a marker substance attached to the polymer. Still other embodiments provide for a marker substance selected from the group consisting of nonfluorescent dyes, fluorescent dyes, radioisotopes, electron opaque substances, enzymes, a second immunological homolog of differing specificity than the first immunological homolog and microspheres. Preferred embodiments provide for a water-soluble polymer selected from the group consisting of polyacrylic acid, polymethacrylic acid, polyacrylamide, polyvinylalcohol, polyallylalcohol, polymer combinations of the foregoing, hydroxyethyl cellulose, hydroxypropyl cellulose, natural water-soluble polymers and synthetic water-soluble polymers.

BRIEF DESCRIPTION OF THE DRAWINGS

Further objectives and understanding of the present invention will become apparent upon reference to the drawings wherein:

FIG. 1 is a stylized view of the preferred embodiment showing an immunoglobulin having attached thereto a water-soluble polymer carrying a marker substance other than a microsphere;

FIG. 2 illustrates an alternative embodiment of the present invention employing a microsphere as a marker substance;

FIG. 3 shows a stylized view of an immunoglobulin attached by the use of biotin-avidin to a water-soluble polymer having microsphere marker substances;

FIG. 4 is a stylized view of an embodiment of the present invention for the detection of a cell surface antigen;

FIG. 5 is a stylized view of a solid-phase antigen detection system for poly-valent antigens using an embodiment of the present invention; and FIG. 6 is another stylized view of a solid-phase antigen detection system using the water-soluble polymer having a marker substance and attached to the antigen of interest.

DETAILED DESCRIPTION OF THE INVENTION AND PREFERRED EMBODIMENTS

In accordance with the stated objects, the preferred immunological substance detection reagent as shown in FIG. 1 is provided having an immunological homolog, here an immunoglobulin 1, specific for an immulogical substance, here an antigen, to be detected 30. As will be noted by those skilled in the art, the stylized component representations in the Figures have been significantly altered as to relative proportions as well as appearance for the sake of clarity. Also to be noted is that discussion pertaining to one figure may be equally applicable to other figures with the exception of different marker substances present or application in different assay systems. The immunoglobulin 1 is attached to a water-soluble polymer 2 having attached thereto a plurality of marker substances 3. Marker substances 3 are preferably fluorescent dyes although other marker substances such as nonfluorescent dyes, radioisotopes, electron opaque substances, enzymes, or a second homolog of differing specificity than the first homolog, may be used in substitution. Still alternatively, fluorescent-containing microspheres 4 could be used as shown in FIG. 2. Also shown in FIG. 2 is use of the reagent in a solid-phase immunoassay wherein the antigen 30 to be detected is immobilized on the surface of a substrate 51.

With reference to FIGS. 1 and 2, the water-soluble polymer 2 is advantageously chosen so as to avoid nonspecific binding to the cell, thereby permitting greatest sensitivity and immunological response. Consequently, those polymers which are cationically charged and therefore tend to attach nonspecifically are preferably avoided. Typical of such preferably avoided, cationically charged polymers are the primary amine-containing polymers.

The preferred water-soluble polymers have an anionic (negative) or zero charge and are ideally chosen from the group consisting of polyacrylic acid, polymethacrylic acid, polyacrylamide, polyvinylalcohol, polyallylalcohol, any of the various possible polymer combinations of these, hydroxyethyl cellulose, hydroxypropyl cellulose, natural water-soluble polymers as well as synthetic water-soluble polymers. It is noted, however, that many of the marker substances 3, 4 tend to be cationically charged, especially the dye-type marker substances. Since this tends to increase unwanted nonspecific binding, the water-soluble polymer may be advantageously adjusted to increase its anionic character and thereby compensate for the increased nonspecific 'staining' characteristic detrimental to desired sensitivity.

The water-soluble polymer, typically having a molecular weight in the range of 1,000 to 100,000,000 daltons, provides the capability of attaching numerous dye-type substances to an antibody having a desired specificity. Of great importance is that the attachment is at a sufficient distance from the antibody in order to avoid deleterious effects on the antibody's reactivity. All these considerations become particularly important when dealing with the long wavelength or red light excited fluorescent dyes which characteristically often exhibit diminished fluorescence in comparison to other dyes such as fluorescein or acridine orange. Consequently, by loading up the water-soluble polymer 2 with numerous dye molecules 3, a gain in sensitivity is accomplished since there is provided a greater concentration of fluorescence thereby enabling presently available automated instrumentation to record more readily the presence of an immunological reaction.

The water-soluble polymer additionally exhibits advantages when used with an enzyme-marker system. Enzymes, like immunoglobulins, are large proteins with an active site which is sensitive to steric hindrance. Direct attachment between an immunoglobulin and an enzyme, although permitting the detection of an immunological reaction between an immunological substance and its homolog following the addition of the substrate, has a disadvantageously low sensitivity due to steric hindrance. The advantageous employment of a water-soluble polymer to connect the immunoglobulin to single or multiple enzyme molecules permits each protein to act in the desired fashion unhindered by the presence of the other. As a result, the immunoassay reagent exhibits increased sensitivity in the detection of the immunological substance.

The invention shows additional utility in conjunction with monoclonal antibodies directed against specific tissue or tumor cell associated antigens. The polymer is capable of carrying an increased load of therapeutic treatment substances or agents above that possible only by employment of direct attachment of the agent to the immunoglobulin itself and further, decreases the chance of denaturation of the immunoglobulin by attachment of the agent. As a result, a monoclonal antibody, attached to a water-soluble polymer carrying chemical, vitamins, drugs, radiochemical treatment molecules or other material desired to be delivered to a specific or targeted site, will be able to localize and specifically attack tumor cells and advantageously provide increased concentrations of the treatment material directly to the targeted site.

It is preferred that a biocompatible polymer be employed in the present invention. Biocompatible means that the polymer is chosen, to avoid producing adverse toxic effects, and to avoid nonspecific binding to cells or the formation of lattice-type structures yielding agglutination-type aggregates. Consequently, preferred embodiments employ polyacrylic acid and polyacrylamide, both polymers being formed from water-soluble monomers polymerized by a free-radical process although anionic/cationic polymerization and condensation methods may also be used. Additionally, it has been found advantageous to employ monomers having functional groups to produce the polymer so that the functional groups may be later utilized to react with a marker substance such as a dye, or immunologic substance. Examples of such monomers having functional groups include acryloyl chloride. The polyacryloyl chloride produced has an active chlorine atom capable of reacting with a primary amine to form an amide linkage. To be noted, however, is that the functional groups are not restricted and other groups including, but not limited to, hydroxyl thiocyanate, isothiocyanate, sulfonyl chloride, succinimide, and dichlorotriazinyl may be employed in substitution.

In accordance with organic procedures well known, it may be necessary to warm the dye and/or put it in the presence of a catalyst in order to stimulate its reaction with the functional group on the polymer. The amount of dye added to the polymer may be advantageously regulated by controlling the concentration ratios or by utilizing different functional groups, one for the dye and one for the antibody. This, of course, is made possible by the fact that the dye typically has only one functional group reactive site to react with the polymer.

In accordance with known skills, other methods which may be advantageously employed to attach the marker substances to the polymer include (a) utilizing an activated group on the marker substance, (b) employing an external activating reagent, (c) in those marker substances having a first portion and a second portion, polymerizing the monomer having the first portion attached to form the polymer, and then adding the second portion for attachment to the first portion, and (d) copolymerization of the marker substance with the monomer.

FIG. 3 demonstrates the utilization of avidin 6-biotin 5 complex in order to effectuate the linking of immunoglobulin 1 to polymer 2 carrying, in this case, microspheres 4. The polymer could just as easily be the carrier of a different marker-type substance such as a dye or other member selected from the marker substance group previously described. Biotin-avidin may be advantageously employed because of its unusually strong binding characteristics, its chemical stability, and sensitivity amplification. The biotin 5 is easily attached to the immunoglobulin by methods well known, and because of its small size, has little or no effect upon the reactivity of the immunoglobulin and further, several may be attached to the antibody to yield increased sensitivity. In contrast to biotin, the avidin molecule is considerably larger and in the past has been utilized to directly carry fluorescein and other dye-type materials. However, the present invention advantageously employs avidin merely to couple the polymer to the antibody. Since the polymer is capable of carrying far more fluorescein or other dye-type material than avidin, the result is a greater concentration of dye associated with the immunological homolog which in turn provides greater sensitivity. Although it is difficult to ensure that only one polymer molecule is attached per avidin molecule, in compensation, the biotinilation of antibodies can be controlled more precisely.

FIG. 4 demonstrates the utilization of the present invention in the determination and localization of an immunological substance or antigenic site 21 on a cell surface 20 by the use of the immunological homolog or immunoglobulin 1 having attached thereto biotin 5. The biotin physically adsorbs to avidin 6 attached to the water-soluble polymer 2 which, in turn, is capable of carrying marker substances 3. With those reagents employing biotin-avidin, it is preferred that just the biotinylated antibody is first reacted with the antigens and then the avidin coupled portion of the reagent is added.

The flexibility of the present invention is further illustrated in FIG. 5 wherein a stylized view of a solid-phase immunoassay is demonstrated. An immunoglobulin 1, sensitive for the antigen to be detected 71, is immobilized on a surface 51 and the sample containing the antigen is contacted with the immobilized immunoglobulin surface. Subsequently the reagent of the present invention, having an immunoglobulin 1 sensitive for the antigen and attached to a polymer 2 having marker substances 3 is washed over the surface. Quantifying the fluorescence or presence of other marker substance will permit direct calculation as to the quantity of antigen present and its precise localization. In the expanded view, the marker substance is an enzyme 40 which is reactive with substrate 41 and breaks it down to 42 and 43 which may be individually detected.

FIG. 6 further demonstrates the enormous flexibility of the present invention and shows the attachment of a water-soluble polymer 2 carrying marker substances 3 to an antigen 80 which thereupon may be contacted with an immunoglobulin 1 specific for the antigen and which immunoglobulin may be immobilized on the surface 51 or may in turn be attached to another polymer carrying marker substances. Further, there may be present unlabelled antigens 80 and an inhibition-type assay employed utilizing methods well-known in the art.

It is to be understood that, as implied by the use of the terms immunological substance and immunological homolog, in many cases, the polymer carrying the marker substances can be attached to the antigen to form a reagent capable of detecting the presence of an antibody immobilized on the surface of a cell or substrate or present in an aqueous solution.

It is further to be understood that many other alternatives or combinations of components will occur to those skilled in the art without departing from the spirit or scope of the invention.

EXAMPLE 1

A copolymer, of approximately 50% (by weight) acrylic acid and 50% (by weight) acrylamide and containing one fluorescent monomer per 100 nonfluorescent monomers, was produced by dissolving the monomers in dimethylformamide (DMF) and adding 2.5% (by weight of monomer) 4,4'-Azobis(4-cyano-valeric acid), as an initiator, and polymerizing for 16 hours at 65° C. under nitrogen. The fluorescent monomer was produced by reacting fluoresceinamine and acryloyl-chloride in equimolor amounts at room temperature. After polymerization, the nonpolymerized components were removed by gel filtration on Biogel P-10 in anhydrous formamide. Fifteen mg of fluorescent polymers were activated by treating the polymer with 34 mg of carbonyl diimidazole (amount equal to 2× the available number of carboxyl groups) and allowing it to react for 30 minutes at room temperature. Sixty mg of N-Hydroxysuccinimide (5× the available number of carboxyl groups) were added and allowed to react at room temperature for 30 minutes. The resulting polymer containing succinimide ester was concentrated by precipitation with anhydrous acetone and, after washing with acetone, was stored in acetone.

For the monoclonal antibody experiments, 1 mg of activated polymer was dried with nitrogen. One-half ml of sodium borate (0.125 M) and 200 μg of OKT3 (T-cell directed monoclonal antibody available from Ortho Pharmaceutical Corporation, Route 202, Raritan, N.J.) in 100 μl phosphate buffered saline were added to the water-soluble polymer and the mixture was incubated for 30 minutes at room temperature. The resulting OKT3-polymer was assayed using the Ortho protocol for T-cell enumeration (this protocol is incorporated by reference and available from Ortho Diagnostic Systems Inc., Route 202, Raritan, N.J.). Essentially the procedure comprises the following: whole blood is reacted with fluorescently labelled antibody. Following lysis of the red cells with an ammonium chloride based lysing reagent, lymphocytes are distinguished from other leucocytes by their forward and 90° light scatter characteristics. The ORTHO SPECTRUM III TM flow cytometer (available from Ortho Diagnostic Systems) collects fluorescence data and identifies lymphocytes by their characteristic light scatter as specified above. This provides a histogram display in which labelled versus unlabelled lymphocytes can be distinguished and enumerated. Assayed in this manner, polymer-OKT3 showed 64% OKT3 positive lymphocytes while conventional OKT3 showed 66% positive lymphocytes (not significantly different). At the same time polymer-OKT3 showed enhanced labelling in that the mean fluorescence was higher and there were many more counts in the highest fluorescence channels.

EXAMPLE 2

Two hundred μg of OKT3 ($1.3 \times 10^{-9}$ moles) was reacted with $2.6 \times 10^{-8}$ moles of biotinyl N-hydroxysuccinimide (2.6 μl in DMF) in a final volume of 200 μl of 0.1 M sodium borate for two hours at room temperature. This treatment introduced a calculated 10 biotin groups per antibody assuming 50% labelling. Meanwhile, 680 μg of purified avidin was added to 2.5 mg of dried, activated fluorescein-polymer prepared as in Example 1 in 200 μl of 0.125 M sodium borate and reacted at room temperature for 1 hour. The avidin was then diluted to 1 ml total volume with phosphate buffered saline. Ten μl of biotinylated OKT3 was mixed with 50 μl of buffy coat ($5 \times 10^5$ leucocytes) and incubated for 30 minutes at room temperature. Following 3 washes with 1.5 ml phosphate buffered saline each to remove non-bound OKT3-biotin, 20 μl of avidin-polymer were added (fluorescein-avidin was also used for comparison purposes) and the mixture was incubated for 30 minutes at room temperature. The samples were washed twice with 1.5 ml phosphate buffered saline each, red cells were lysed as in Example 1, and then analyzed with the ORTHO SPECTRUM III TM as in Example 1. The results showed enhancement of labelling compared to conventionally labelled avidin. This demonstrates that the fluorescent polymer is readily detectable and became covalently bound to avidin which, in turn, then bound successfully to the biotinylated OKT3 on the cell surface.

The skilled man will readily appreciate that other marker substances may be used in substitution for fluorescein under appropriate conditions readily discernible by those skilled in the art.

We claim:

1. An immunological substance detecting reagent comprising:
   (a) an immunological homolog specific for the substance to be detected;
   (b) a water-soluble, substantially noncross-linked and nonprimary amine containing polymer having a net charge not greater than zero; and
   (c) means for attaching substantially only one homolog to each water-soluble polymer.

2. An immunological substance detecting reagent comprising:
   (a) an immunological homolog specific for the substance to be detected;
   (b) a water-soluble polymer-marker substance complex having in combination a net charge not greater than zero, said polymer being nonprimary amine containing and substantially noncross-linked; and
   (c) means for attaching substantially only one homolog to each water-soluble polymer.

3. An immunological substance detecting reagent comprising:
   (a) an immunological homolog specific for the substance to be detected; and
   (b) a water-soluble polymer having a marker substance associated and means for attaching substantially only one homolog to each polymer, the entire polymer-marker-attaching means complex having a net charge not greater than zero, said polymer being nonprimary amine containing and substantially noncross-linked.

4. An immunological substance detecting reagent as provided in claims 1 or 2 wherein the attaching means is selected from the group consisting of activated groups on the homolog, activated coupling reagents, activated groups on the polymer, activatable groups on the polymer, covalent bonds, and biotin-avidin complex.

5. An immunological substance detecting reagent as provided in claim 1 wherein the reagent further comprises a marker substance attached to the polymer.

6. An immunological substance detecting reagent as provided in claims 2, 3, or 5 wherein the marker substance is selected from the group consisting of nonfluorescent dyes, fluorescent dyes, radioisotopes, electron opaque substances, enzymes, a second immunological homolog of differing specificity than the first homolog and microspheres.

7. An immunological substance detecting reagent as provided in claims 1, 2 or 3 wherein the water-soluble polymer is selected from the group consisting of polyacrylic acid, polymethacrylic acid, polyacrylamide, polyvinylalcohol, polyallylalcohol, polymer combinations of the foregoing, hydroxyethyl cellulose, hydroxypropyl cellulose, natural water-soluble polymers and synthetic water-soluble polymers.

8. An immunological substance detecting reagent comprising:
   (a) a first immunological homolog specific for the substance to be detected;
   (b) a water-soluble, nonprimary amine containing and substantially noncross-linked polymer having a charge not greater than zero and selected from the group consisting of polyacrylic acid, polymethacrylic acid, polyacrylamide, polyvinylalcohol, polyallylalcohol, polymer combinations of the foregoing, hydroxyethyl cellulose, hydroxypropyl cellulose, natural water-soluble polymers and synthetic water-soluble polymers; and the polymer further having in association therewith a marker substance selected from the group consisting of nonfluorescent dyes, fluorescent dyes, radioisotopes, electron opaque substances, enzymes, a second immunological homolog of differing specificity than the first homolog and microspheres; and
   (c) means for attaching substantially only one first homolog to each polymer-marker complex.

9. An immunological substance detecting reagent comprising:
   (a) a first immunological homolog specific for the substance to be detected;
   (b) a water-soluble, nonprimary amine containing and substantially noncross-linked polymer selected from the group consisting of polyacrylic acid, polymethacrylic acid, polyacrylamide, polyvinylalcohol, polyallylalcohol, polymer combinations of the foregoing, hydroxyethyl cellulose, hydroxypropyl cellulose, natural water-soluble polymers and synthetic water-soluble polymers, and having in association therewith a marker substance selected from the group consisting of nonfluorescent dyes, fluorescent dyes, radioisotopes, electron opaque substances, enzymes, a second immunological homolog of differing specificity than the first homolog and microspheres, the polymer-marker complex having a net charge not greater than zero; and
   (c) means for attaching substantially only one first homolog to each polymer-marker complex.

10. An immunological substance detecting reagent comprising:
    (a) a first immunological homolog specific for the substance to be detected; and
    (b) a water-soluble, nonprimary amine containing and substantially noncross-linked polymer, selected from the group consisting of polyacrylic acid, polymethacrylic acid, polyacrylamide, polyvinyl alcohol, polyallylalcohol, polymer combinations of the foregoing, hydroxyethyl cellulose, hydroxypropyl cellulose, natural water-soluble polymers and synthetic water-soluble polymers, the polymer having in association therewith a marker substance selected from the group consisting of nonfluorescent dyes, fluorescent dyes, radioisotopes, electron opaque substances, enzymes, a second immunological homolog of differing specificity than the first homolog and microspheres, and the polymer further having in combination therewith means for attaching substantially only one first homolog to each polymer, the entire polymer-marker-attaching means complex having a net charge not greater than zero.

11. An immunological substance detecting reagent as provided in claims 8, 9 or 10 wherein the attaching means is selected from the group consisting of activated groups on the homolog, activated coupling reagents, activated groups on the polymer, activatable groups on the polymer, covalent bonds, and biotin-avidin complex.

12. An immunological substance detecting reagent as provided in claims 2, 3, 5, 8, 9, or 10 wherein the attaching means is a complex of biotin-avidin and the marker substance is a fluorescent dye.

13. A reagent as provided in claim 5 wherein:
    (a) the immunological substance is an antigen present at a site associated with tissue;
    (b) the immunological homolog is an antibody specific for the antigen; and
    (c) the marker substance is substituted with a therapeutic substance selected from the group consisting of chemotherapeutic substances, radiotherapeutic substances, vitamins, tumor-inhibiting drugs, and tissue affecting materials desired to be delivered to the antigenic site.

14. A treatment agent specific for tissue having an associated antigen comprising:
    (a) a water-soluble, nonprimary amine containing and substantially noncross-linked polymer having a net charge not greater than zero;
    (b) an antibody, specific for the antigen, bound to the polymer on a substantially one antibody per polymer basis; and
    (c) a therapeutic substance bound to the polymer and selected from the group consisting of chemotherapeutic substances, radiotherapeutic substances, vitamins, tumor-inhibiting drugs, and tissue affecting materials desired to be delivered to the antigenic site.

15. A treatment agent as provided in claim 14 wherein the water-soluble polymer is selected from the group consisting of polyacrylic acid, polymethacrylic acid, polyacrylamide, polyvinyl alcohol, polyallylalcohol, polymer combinations of the foregoing, hydroxyethyl cellulose, hydroxypropyl cellulose, natural water-soluble polymers and synthetic water-soluble polymers.

16. A treatment agent as provided in claim 15 wherein the antibody is bound to the polymer by bonding means selected from the group consisting of activated groups on the antibody, activated coupling reagents, activated groups on the polymer, activatable groups on the polymer, covalent bonds, and biotin-avidin complex.

* * * * *